(12) United States Patent
Simon et al.

(10) Patent No.: US 10,067,041 B2
(45) Date of Patent: *Sep. 4, 2018

(54) CLEARING AGENT AND MOUNTING MEDIUM FOR MICROSCOPY

(71) Applicant: Rutgers, The State University of New Jersey, New Brunswick, NJ (US)

(72) Inventors: James E. Simon, Princeton, NJ (US); Thomas Villani, New Brunswick, NJ (US); Adolfina Koroch, Highland Park, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 37 days.

This patent is subject to a terminal disclaimer.

(21) Appl. No.: 15/258,474

(22) Filed: Sep. 7, 2016

(65) Prior Publication Data
US 2016/0377514 A1    Dec. 29, 2016

Related U.S. Application Data

(63) Continuation of application No. 14/391,106, filed as application No. PCT/US2013/035761 on Apr. 9, 2013, now Pat. No. 9,464,971.
(Continued)

(51) Int. Cl.
    *G01N 1/30*          (2006.01)

(52) U.S. Cl.
    CPC ......... *G01N 1/30* (2013.01); *G01N 2001/307* (2013.01)

(58) Field of Classification Search
    CPC .................................................... G01N 1/30
    See application file for complete search history.

(56) References Cited

U.S. PATENT DOCUMENTS

| 3,961,097 A | 6/1976 | Gravlee, Jr. |
| 4,120,991 A | 10/1978 | Ornstein et al. |

(Continued)

FOREIGN PATENT DOCUMENTS

| CA | 2198520 A1 | 4/1998 |
| WO | 1994/004906 | 3/1994 |

(Continued)

OTHER PUBLICATIONS

U.S. Appl. No. 14/391,106, filed Oct. 7, 2014, Clearing Agent and Mounting Medium for Microscopy.
(Continued)

*Primary Examiner* — Rosanne Kosson
(74) *Attorney, Agent, or Firm* — Fox Rothschild LLP

(57) ABSTRACT

A clearing agent and mounting solution for microscopy is disclosed comprising (a) trichloroethanol, (b) optionally, trichloroacetic acid, (c) optionally, glycerol and (d) optionally, water, where the refractive index of the solution is greater than or equal to about 1.3810. The solution can further comprise a C1-C6 alcohol, other acids, and/or a stain. The solution can also comprise derivatives and/or analogs of 2,2,2-trichloroethanol and/or trichloroacetic acid. Also disclosed is a method of preparing specimens for microscopy comprising (a) applying a specimen to a microscope slide or a cuvette, (b) applying a quantity of the above solution sufficient to mount the specimen, and (c) optionally applying a cover slip. The solution can be used effectively with stains or dyes, and with fresh, partially dry or dried materials, and for temporary or semi-permanent to permanent mounting. The solution can be used with specimens or tissues/cells/parts originating from animals, poultry, livestock, humans, higher plants, yeasts, molds, microorganisms, insects, mites, or reptiles.

6 Claims, 14 Drawing Sheets

Related U.S. Application Data

(60) Provisional application No. 61/622,210, filed on Apr. 10, 2012.

(56) References Cited

U.S. PATENT DOCUMENTS

| | | |
|---|---|---|
| 6,451,260 B1 | 9/2002 | Dusterhoft et al. |
| 7,569,130 B2 | 8/2009 | Edwards et al. |
| 2007/0134798 A1 | 6/2007 | McCormick et al. |
| 2010/0124750 A1 | 5/2010 | Stocker et al. |

FOREIGN PATENT DOCUMENTS

| | | |
|---|---|---|
| WO | 2009/086487 | 7/2009 |
| WO | 2010/065400 | 6/2010 |

OTHER PUBLICATIONS

Baumgartner et al., "Plant histology as an aid in squirrel food-habit studies," J Wildlife Management 3(3)266-268, 1939.
International Preliminary Report on Patentability for PCT/US2013/035761, dated Oct. 14, 2014.
International Search Report for PCT/US2013/035761, dated Jul. 23, 2013.
Moreira et al., "Kinematic viscosity and refractive index of aqueous solutions of ethanol and glycerol," Ind Eng Chem Res 48:2157-2161, 2009.
Supplementary European Search Report for European Patent Application No. 137752663, dated Oct. 14, 2015.
Written Opinion of the International Search Authority for PCT/US2013/035761, dated Jul. 23, 2013.

| Acidified chloral hydrate solution | Example 1 Clearing agent and mounting solution |
|---|---|
|  |  |
| Fig 8A | Fig 8B |

CLEARING AGENT AND MOUNTING MEDIUM FOR MICROSCOPY

CROSS-REFERENCE TO RELATED APPLICATIONS

This application is a Continuation of U.S. patent application Ser. No. 14/391,106, filed Oct. 7, 2014, which is the U.S. National Phase of International Patent Application Serial No. PCT/US2013/035761, filed Apr. 9, 2013, which claims priority under 35 U.S.C. § 119(e) to U.S. Provisional Patent Application No. 61/622,210, filed on Apr. 10, 2012. The contents of the foregoing applications are incorporated herein by reference in their entireties.

FIELD OF THE INVENTION

The invention is related to the preparation of specimens for microscopy, and particularly to the development of replacements for chloral hydrate as a clearing agent and mounting medium for microscopy.

BACKGROUND OF THE INVENTION

There are different methods for identification of materials including macroscopic, chemical and microscopic identification among others. Microscopic identification is a technique that uses a microscope to identify characteristic features of living organisms, parts of an organism, cells or sub-cellular organs, as well as minerals or other non-living materials. The importance of microscopy resides in the ability to clearly identify differences between organisms or their parts by focusing on specific characteristics or diagnostic structures. Microscopy relies on dependable, readily available reagents as clearing agent and mounting solutions, optionally used in conjunction with stains in order to visualize the materials under the slide.

The general microscopy procedure for specimens derived from living organisms comprises mounting a small sample of the tissue to be analyzed in a solvent solution and observing it under the microscope. In many cases the cell contents obscure the tissues, making it difficult to identify characteristic features. Differences in refractive index within the specimen prohibit visualization of deeper visual planes, and occlude detail from observation. In these cases a clearing solution is applied in order to improve the transparency of the specimen, allowing one to visualize multiple vertical layers of the specimen without careful sectioning or remounting. This increased transparency and improved clarity allows the microscope user to visualize across a full range of vertical planes in the sample, allowing the user to select interesting focal planes by adjusting the focus.

A valuable and almost universally used clearing agent for microscopy is acidified chloral hydrate glycerol solution (chloral hydrate solution acidified with hydrochloric acid), also known as Hertwig's solution. Acidified chloral hydrate solution is used in botanical microscopy, mycology, entomology, histology, mineralogy, food science, quality control, forensics, nematology, archeology, paleontology, virology, immunology, microscopy including but not limited to differential interference contrast microscopy, electron microscopy, fluorescence microscopy, confocal microscopy, and other related applications of microscopy and optics. Chloral hydrate when applied to botanical samples dissolves cellular contents and intercellular substances thus allowing cell walls and shapes of the cells to be easily observed. Chloral hydrate solution has a high refractive index, which improves its transparency over media with lower refractive indices (such as water).

Many Pharmacopeias contain published protocols for microscopic authentication analyses of herbal preparations using acidified chloral hydrate as the clearing agent. Consequently, chloral hydrate has become the industry standard and an important reagent required on a daily basis for many laboratories focused on quality assessment of herbal products. For example, in botanical samples, chloral hydrate is used to assist in the identification of cells with suberized cell walls, fibers (an elongated cell with thick cell walls at maturity that gives strength and support to the plant tissue), vessel elements (a tube-like series of cells with wide lumen and perforated walls), trichomes (hair-like structures that project from the epidermal surface of the leaves, flowers and stems), stoma (pores in the epidermis of the leaf through which the plant exchanges gases) and pollen.

Chloral hydrate, the key component in acidified chloral hydrate solution, is considered under US law to be a narcotic hypnotic, and as such is a DEA (Drug Enforcement Administration) scheduled substance, requiring DEA approval and compliance in order to purchase and/or possess it. This has precluded scientists from being able to purchase this reagent; and in particular has precluded academic institutions (elementary schools, middle schools, high schools, colleges and universities) from purchasing this almost universal reagent that is required for preparing slides across all disciplines—from plant science, to biological sciences, to medical sciences and more. Furthermore, maintaining DEA compliance is a costly, tedious, and time-consuming process.

Thus, a major disadvantage of using acidic chloral hydrate-glycerol solution is that chloral hydrate is a controlled substance and requires a special permit in order to purchase, possess, or use in the US. Therefore cost-effective, readily available and unregulated replacements for acidified chloral hydrate solution are needed as clearing and mounting agents for microscopy.

BRIEF SUMMARY OF THE INVENTION

It has now been discovered that aqueous solutions of trichloroethanol, or its derivatives or analogs, with or without other additives, can effectively replace acidified chloral hydrate solution as a clearing and mounting medium for microscopy.

One embodiment of the present invention is directed to novel chemical solutions for clearing and mounting tissues for microscopic identification which overcomes the above-identified issues with acidified chloral hydrate solution, without sacrificing the quality and resolution of the images observed. Another embodiment of the invention is directed to methods of preparing specimens for microscopy using the clearing agent and mounting solution.

One embodiment of the invention is directed to a clearing agent and mounting solution including a permanent mount for microscopy comprising:
  (a) about 10% to about 97% (v/v) of trichloroethanol;
  (b) 0% to about 50% (v/v) of trichloroacetic acid;
  (c) 0% to about 50% (v/v) of glycerol; and
  (d) optionally, water;
wherein the refractive index of said solution is greater than or equal to about 1.3810.

Preferably the refractive index is about 1.3810 to about 1.4880.

Preferably trichloroethanol is present in about 34.5% to about 97%; more preferably in about 55% (v/v). Preferably trichloroacetic acid and glycerol are present in 0% to about 5%, and 0% to about 12.5%, respectively.

In one particular embodiment, the clearing agent and mounting solution contains trichloroethanol in about 56.25% (v/v), trichloroacetic acid in about 1.25% (v/v), glycerol in about 12.5% (v/v), and water in about 30% (v/v).

The clearing agent and mounting solutions can further comprise one or more of the following:
1. a C1-C6 alcohol in about 5-85% (v/v), for example methanol and/or ethanol in about 25-30%;
2. an inorganic acid selected from the group consisting of hydrochloric acid, sulfuric acid, phosphoric acid, and mixtures of two or more thereof;
3. a stain or dye selected from the group consisting of carmine, carmine, crystal violet, gram stain, aniline blue, phoroglucinol, lactophenol, sudan IV, iodine/potassium iodide stain, eosin and fuchsin;
4. a dissolved plastic polymer or resin;
5. monomeric units, polymerization of which stabilizes a mounting medium and/or specimen;
6. one or more C1-C12 organic acids, which can be selected from the group consisting of acetic acid, formic acid, lactic acid and citric acid;
7. a chemical preservative, which preserves the integrity of the specimen or extends its working and viewable lifetime;
8. a salt solution or buffer, which can be selected from the group consisting of phosphate, citrate, acetate, tris or other water-soluble buffers;
9. an alkaline hydroxide base, which can be selected from the group consisting of sodium hydroxide, calcium hydroxide, potassium hydroxide, magnesium hydroxide and lithium hydroxide;
10. a compound selected from the group consisting of ethylene glycol, polyethylene glycols and derivatives thereof;
11. polyvinylpyrrolidone dissolved in an organic solvent selected from the group consisting of ethanol, methanol, isopropanol, acetone, and mixtures of two or more thereof;
12. compounds selected from the group consisting of derivatives and analogs of 2,2,2-trichloroethanol, and derivatives and analogs of 2,2,2-trichloroacetic acid;
13. acidic and/or basic additives to alter pH and/or the salt concentration of the solution;
14. compounds to influence the digestive capacity of the reagent;
15. a solidification aid selected from the group consisting of polyethylene glycol, polyamide resin, polyvinylpyrrolidone, polyvinylalcohol and mixtures of two or more thereof;
16. an aromatic solvent selected from the group consisting of xylene, toluene, other benzene derivatives and mixtures of two or more thereof;
17. dimethylsulfoxide;
18. an oil selected from the group consisting of cedar oil, pine oil, peanut oil, other plant-derived oils and mixtures of two or more thereof;
19. a dried exudate obtained from the stems and branches of trees and/or plants containing saccharide-based gums, such as Arabic gum;
20. a carbohydrate selected from the group consisting of mono-, di- and poly-saccharide forms of C4-C6 carbohydrates and mixtures of two or more thereof;
21. an aqueous solution of an amino acid or mixtures of two or more amino acids.

Another embodiment of the invention is directed to a clearing agent and mounting solution for microscopy comprising:
(a) about 10% to about 97% (v/v) of a trichloroethanol derivative or analog;
(b) 0% to about 50% (v/v) of a trichloroacetic acid derivative or analog;
(c) 0% to about 50% (v/v) of glycerol;
(d) optionally, water; and
(e) optionally, 5-85% (v/v) of a C1-C6 alcohol;
wherein the refractive index of said solution is greater than or equal to about 1.3810; wherein said trichloroethanol derivative or analog is selected from the group consisting of mono- and poly-halogenated branched and unbranched alcohols, diols, glycol aldehydes, aldehyde-hydrates, hemi-acetals, acetals, ketals, aminals, hemi-aminals of at least 2 carbon units, and polymeric embodiments thereof; wherein the branches comprise mono- or poly-halogenated aliphatic or aromatic groups containing hydroxyl, amino, ether, carboxyl, carboxyamido, carbonate, carbamyl, carbonyl-chloride, polyethylene-glycol, or aminoethanol groups.

Another embodiment of the invention is directed to a clearing agent and mounting solution for microscopy comprising:
(a) about 10% to about 30% (v/v) of trichloroacetic acid;
(b) about 10% to about 30% (v/v) of sodium hydroxide; and
(c) optionally, water,
wherein the refractive index of said solution is greater than or equal to about 1.3810.

A further aspect of the invention is directed to a method of preparing specimens for microscopy comprising:
(a) applying a specimen to be examined to a microscope slide or a cuvette;
(b) applying a sufficient quantity of an inventive clearing agent and mounting solution to mount said specimen; and
(c) optionally, applying a cover slip.

1-100 drops of the clearing agent and mounting solution can be applied.

In another embodiment, the method of preparing a specimen for microscopy comprises:
(a) soaking a specimen in sufficient quantity of an inventive clearing solution for at least 1 minute to about 12 months to provide a cleared specimen,
(b) applying the cleared specimen to a microscope slide, cuvette, or well for observation, and
(c) optionally, applying a cover slip.

Alternatively, after soaking the specimen, the cleared specimen can be applied to a resin which will solidify, and then be cast into a solid for examination or indefinite storage.

Alternatively, after soaking the specimen, a solution of 5-20% polyvinylpyrrolidone in methanol can be applied to the cleared specimen, which is optionally, dried at 50-90° C. until hardened.

Alternatively, after soaking the specimen, a stain or dye can be applied to the cleared specimen to provide a cleared stained specimen whereby the features of the specimen are selectively highlighted; the cleared stained specimen can be applied to a microscope slide, cuvette, or well for observation, and optionally covered with a cover slip. The stain or dye can be a fluorescent stain or dye, so that the cleared stained specimen can be visualized using a fluorescent and/or epifluorescent and/or confocal microscope Another aspect of the invention is directed to a method of preparing a specimen for spectrophotometric analysis comprising:
(a) applying a specimen to a cuvette; and
(b) applying a sufficient quantity of an inventive clearing agent and mounting solution to mount said specimen.

Another aspect of the invention is directed to use of an inventive clearing agent and mounting solution to remove pigment, dye, stain, or color from a specimen.

A further aspect of the invention is directed to use of an inventive clearing agent and mounting solution to remove excess stain or dye and to increase the contrast of particular structures and/or organisms within a specimen.

Another aspect of the invention is directed to use of an inventive clearing agent and mounting solution to increase the transparency of a specimen and to allow multiple vertical planes to be visualized without the need to section, remount, or further modify the specimen.

Yet another aspect of the invention is directed to use of an inventive clearing agent and mounting solution to simultaneously dehydrate, depigment, and clear specimens for microscopic and/or visual analysis.

DETAILED DESCRIPTION OF PREFERRED EMBODIMENTS

Figure 1:
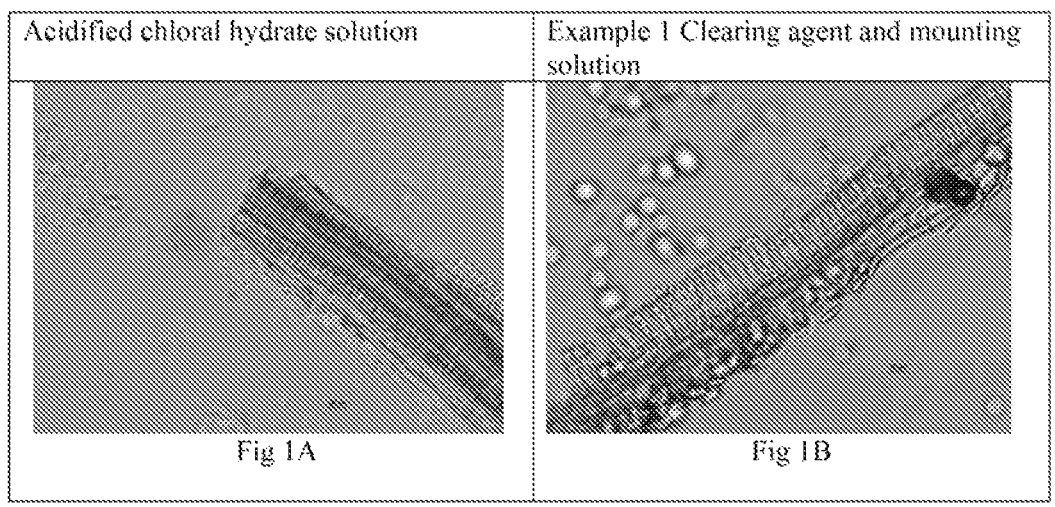
FIG. 1 shows a microscopic view of characteristic annular vessel elements and fibers of ginger, *Zingiber officinale* Roscoe (Zingiberaceae); comparison of acidified chloral hydrate solution versus Example 1 solution.

With this invention, it has now been discovered that aqueous solutions of trichloroethanol, or its derivatives or analogs, with or without other additives, can effectively replace acidified chloral hydrate solution as a clearing and mounting medium for microscopy for both living and nonliving organisms and nonliving materials. One embodiment of the present invention is a substitute for acidified chloral hydrate glycerol solution, wherein the solution components, for example trichloroethanol, are inexpensive, easy to acquire, do not require a DEA license to possess and use, and greatly reduce the risk involved in operations which formerly depended on the use of chloral hydrate. The inventive solutions possess a high refractive index (greater than or equal to about 1.3810; preferably about 1.3810 to about 1.4880; most preferably about 1.4315 to about 1.4880), preferably higher than acidified chloral hydrate solution (1.4280), which results in clearer, and equivalent or higher quality viewing under a microscope. High refractive indices are required for clear viewing of objectives in microscopy, as materials with a high refractive index are more transparent. As a reference, the refractive index of borosilicate (Pyrex) glass is 1.470. Thus, several of the embodiments of the clearing agent and mounting solution of the invention have refractive indices higher than that of glass. It has been discovered that trichloroethanol, or its derivatives or analogs, admirably meet the above-identified criteria as replacements for chloral hydrate.

Use of the clearing agent and mounting solution of the invention helps to macerate and digest clusters of cellular material, and helps to clarify and increase transparency of those tissues, minerals, elements of interest in microscope slides. This solution is an effective immersion medium, and useful in all types of fixative preparations and as an effective dehydration agent. The clearing compound and/or its derivatives can also be used as a semi-permanent or permanent mount, allowing one to visualize specimens days or even months later. This clearing compound and/or its derivatives can also be used with any stains, allowing one to further visualize specimens and components within specimens.

Description of the Clearing Agent and Mounting Solutions and Applications

This invention encompasses the identification of chemical compounds that have not heretofore been used in microscopy applications. In one embodiment, the clearing agent and mounting solution of the invention comprises any concentration of 2,2,2-trichloroethanol, or derivatives or analogs thereof, and/or 2,2,2-trichloroacetic acid, or derivatives or analogs thereof in water and/or glycerol and/or alcohol solution, mixed for the purpose of clearing and/or mounting media for microscope/optical use.

For the purposes of the present invention, the term "derivative" means a chemical compound which still retains the parent structure as a substructure, and can be chemically derived from the parent (e.g., trichloroethanol or trichloroacetic acid). For example, with 2,2,2-trichloroethanol as the parent, a derivative would retain the 2,2,2-trichloroethoxy substructure, such as is found in the corresponding acetate (1-acetoxy-2,2,2-trichloroethane, alternatively named 2,2,2-trichloroethylacetate) or the methyl ether (1-methoxy-2,2,2-trichloroethane) derivatives.

Figure 10:
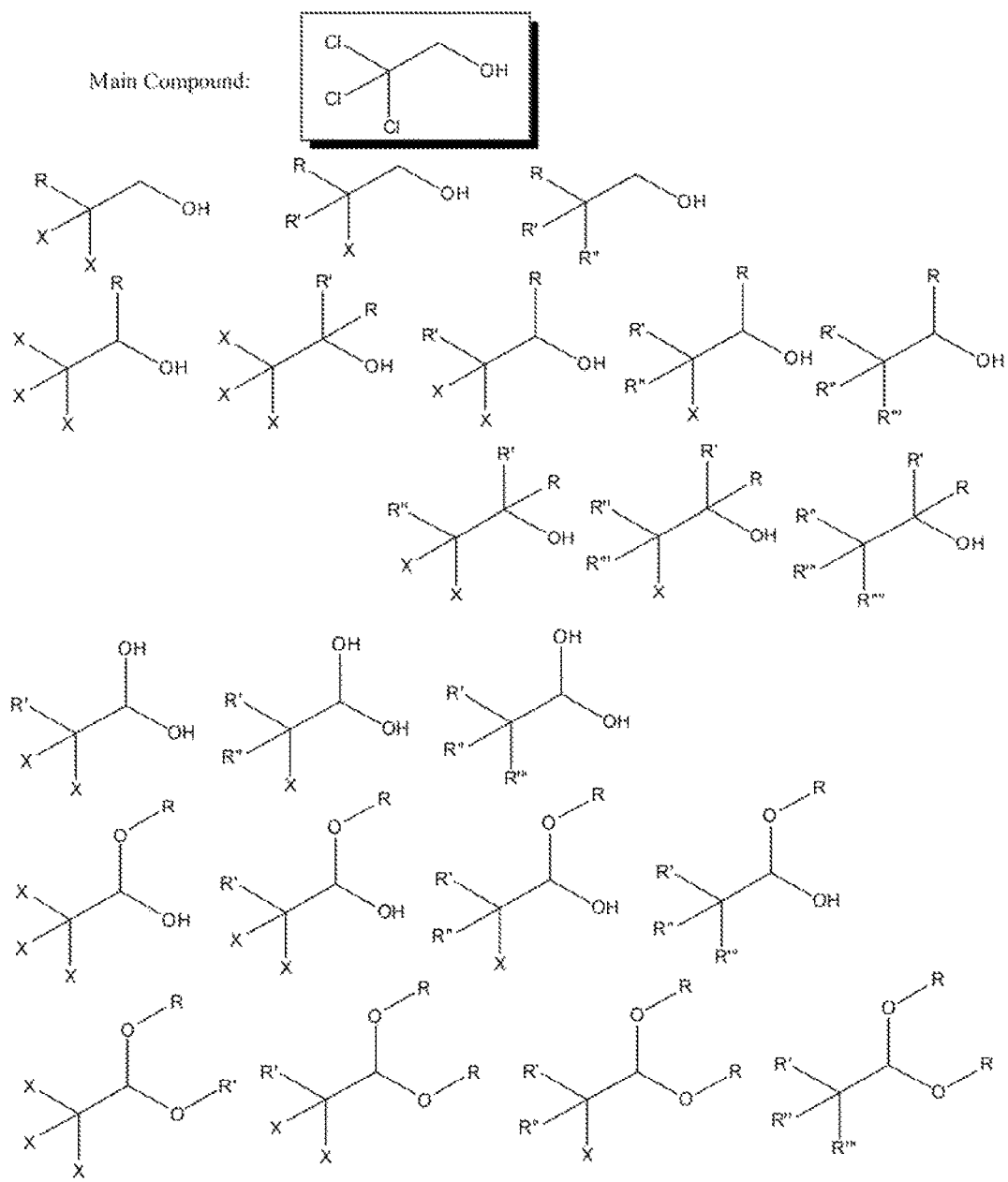
FIG. 10 discloses the chemical structures of analogs of 2,2,2-trichloroethanol useful for preparation of clearing agent and mounting solutions of the invention.

Also for the purposes of the present invention, the term "analog" means a chemical compound in which the core structure of the parent is changed or further substituted, as is commonly known in the medicinal chemistry arts. For example, the change can include replacement of atoms or groups with other atoms or groups (isosteres). Examples of analogs of 2,2,2-trichloroethanol are displayed in FIG. 10.

In one preferred embodiment, the clearing agent and mounting solution of the invention comprises trichloroethanol and/or its analogs or derivatives. In another preferred embodiment, the clearing agent and mounting solution comprises both trichloroethanol and/or its derivatives or analogs, and trichloroacetic acid and/or derivatives or analogs. One particularly preferred embodiment of the invention is directed to a clearing agent and mounting solution for microscopy comprising:

(a) about 10% to about 97% (v/v) of trichloroethanol;
(b) 0% to about 50% (v/v) of trichloroacetic acid;
(c) 0% to about 50% (v/v) of glycerol; and
(d) optionally, water;

wherein the refractive index of said clearing agent and mounting solution is greater than or equal to about 1.3810, preferably about 1.3810 to about 1.4880, most preferably about 1.4315 to about 1.4880. The clearing agent and mounting solution can optionally further contain a C1-C6 alcohol, another acid, such as hydrochloric acid, and/or a dye or stain for visualizing various components of the specimen. Preferably trichloroethanol is present in about 34.5% to about 97%. Preferably trichloroacetic acid is present in 0% to about 5%. Preferably glycerol is present in about 0% to about 12.5%. The glycerol can be supplemented or replaced entirely with one or more compounds selected from the group consisting of ethylene glycol, polyethylene glycols and derivatives thereof.

Preferably the clearing agent and mounting solution comprises about 34.5% to about 97% trichloroethanol, 0% to about 5% trichloroacetic acid, and 0% to about 12.5% glycerol. In one particularly preferred embodiment, the clearing agent and mounting solution contains trichloroethanol in about 56.25% (v/v), trichloroacetic acid in about 1.25% (v/v), glycerol in about 12.5% (v/v), methanol in about 25%, and water in about 5% (v/v).

A further embodiment of the clearing agent and mounting solution of the invention comprises trichloroacetic acid and/or derivatives without trichloroethanol and/or derivatives. One preferred clearing agent and mounting solution consists of an aqueous glycerol solution of trichloroethanol and trichloroacetic acid (Example 1). The trichloroacetic acid can be supplemented or replaced entirely with hydrochloric acid and/or sulfuric acid. One preferred clearing agent and mounting solution consists of an aqueous glycerol solution of trichloroethanol and hydrochloric acid. The 2,2,2-trichloroethanol analog, 2-chloroacetaldehyde dimethyl acetal, FIG. 10, also serves as an effective clearing agent. The clearing agent and mounting solution can include derivatives of 2,2,2-trichloroethanol and/or 2,2,2-trichloroacetic acid created by adding/adjusting the concentration of buffer, and/or acidic/basic additives intended to alter pH and/or salt concentration of the solution; and/or compounds to increase/decrease the digestive capacity of the reagent; and/or any additives intended to preserve specimens/samples; and/or any additives intended for dying or staining applications.

With regard to the alcohol (other than trichloroethanol or derivatives), the clearing agent and mounting solutions can comprise one or more C1-C6 alcohols, for example ethanol, 1-propanol, 2-propanol or t-butanol.

The clearing agent and mounting solutions can also further comprise:

a dissolved plastic polymer, such as polyvinylpyrrolidone, polypropylene, polyethylene, polyether, polyamide; and/or
monomeric units which are subsequently polymerized in order to stabilize a mounting medium and/or specimen; and/or
one or more C1-C12 organic acids, such as formic acid, acetic acid, lactic acid, ascorbic acid, gallic acid, benzoic acid, toluic acid, p-hydroxybenzoic acid or citric acid; and/or
a chemical preservative; and/or a salt of phosphate, citrate, acetate, tris, or other water-soluble buffers; the buffer can be added as an aqueous solution; and/or alkaline hydroxide base, such as sodium hydroxide, calcium hydroxide or lithium hydroxide; the base can be added as an aqueous solution. The inventive clearing agent and mounting solution and/or its derivatives and/or its analogs can also be used with commercial and noncommercial stains just as effectively as current clearing agents.

The present invention also encompasses various derivatives and/or analogs of 2,2,2-trichloroethanol including mono- or poly-halogenated branched or unbranched alcohols, diols, glycols, aldehydes, aldehyde-hydrates, hemiacetals, acetals, ketals, aminals, and hemi-aminals of at least 2 carbon units, where branches are defined as any mono- or poly-halogenated aliphatic or aromatic side chains containing hydroxyl, amino, ether, carboxyl, carboxyamido, carbonate, carbamyl, carbonyl-chloride, polyethyleneglycol, or aminoethanol groups, and any polymeric embodiment of such derivatives.

Derivatives and analogs of 2,2,2-trichloroacetic acid include mono- or poly-halogenated branched or unbranched carboxylic acids, carbamates, amides, and carbonates of at least 2 carbon units, where branches are defined as any mono- or poly-halogenated aliphatic or aromatic side chains containing hydroxyl, amino, ether, carboxyl, carboxyamido, carbonate, carbamyl, carbonyl-chloride, polyethylene-glycol, or aminoethanol groups, and any polymeric embodiment of such derivatives.

Thus, a further embodiment of the invention is directed to a clearing agent and mounting solution for microscopy comprising:

(a) about 10% to about 97% (v/v) of a trichloroethanol derivative or analog;

(b) 0% to about 50% (v/v) of a trichloroacetic acid derivative or analog;

(c) 0% to about 50% (v/v) of glycerol; and (d) optionally, water;

wherein the refractive index of said solution is greater than or equal to about 1.3810; wherein said trichloroethanol derivative or analog is selected from the group consisting of mono- and poly-halogenated branched and unbranched alcohols, diols, glycols, aldehydes, aldehyde-hydrates, hemi-acetals, acetals, ketals, aminals, and hemi-aminals of at least 2 carbon units, and any polymeric embodiment of such derivatives; where branches are defined as any mono- or poly-halogenated aliphatic or aromatic side chains containing hydroxyl, amino, ether, carboxyl, carboxyamido, carbonate, carbamyl, carbonyl-chloride, polyethylene-glycol, or aminoethanol groups.

Another embodiment of the invention is directed to a method of preparing a specimen for microscopy comprising:

(a) applying a specimen to be examined to a microscope slide, well, or cuvette;

(b) applying a sufficient quantity of the clearing agent and mounting solution of claim 1 to clear and mount said specimen; and (c) optionally, applying a cover slip.

1-100 drops, preferably about 2 drops of the clearing agent and mounting solution are applied to the specimen on the slide in order to fix/mount the specimen. The specimen can be further protected with a cover slip.

A related embodiment is directed to a method of preparing a specimen for spectrophotometric analysis comprising:

(a) applying a specimen to a cuvette or well; and (b) applying a sufficient quantity of the clearing agent and mounting solution of claim 1 to clear said specimen (1-10× volume of sample).

As discussed above the present invention is directed to the use of non-chloral hydrate clearing and mounting compounds of appropriate refractive index for novel applications in microscopy. Given the current shortage and limitation of access to the commercial universally-used clearing agent (acidified chloral hydrate), the present invention provides to consumers and the general public a method that can replace the currently used clearing agent, and provides a method accessible to those who are no longer able to purchase the regulated compound chloral hydrate. Thus, the clearing reagents and methods of the present invention are of immediate commercial value and of significant impact because both scientists and manufacturers have been seeking to find a replacement for chloral hydrate in microscopy and other optical applications. The clearing reagents and methods of the present invention are also of immediate commercial value and of significant impact because they can be used with any stains as well as for semi-permanent and permanent mounting.

Optical Properties

One embodiment of the invention comprises a solution which increases the apparent transparency of an objective in microscopy/optical techniques by increasing the refractive index of the medium in which said objective is suspended/immersed. Refractive index of a material is a dimensionless quantity which represents the way light propagates through the material. The refractive index is defined as the factor by which the wavelength and the velocity of the radiation with respect to in a vacuum. The refractive index of a material is closely related to its dielectric constant, and therefore to its transparency. The refractive index n of a material is given by the following equation:

$$n = \sqrt{\frac{\sqrt{\epsilon_1^2 + \epsilon_2^2} + \epsilon_1}{2}},$$

where $\epsilon_1$ and $\epsilon_2$ represent the real and imaginary parts of the dielectric constant, respectively. Materials which have a high dielectric constant contain multiple lone pairs of electrons and/or electronegative elements, which give them a high degree of polarizability, the property which is expressed by the dielectric constant. A high degree of polarizability allows for an electromagnetic wave to propagate easily through the material, since as the electromagnetic wave propagates through the material, it will induce a localized electromagnetic field. It is useful to use the analogy of waves through liquids, the less viscous and easier the liquid is to move (by analogy related to higher polarizability), the easier a wave can propagate through without losing energy from absorption. In electromagnetic waves, a high polarizability corresponds to this "easier movement" of the wave through the material, which results in less absorption of the wave by the material. Therefore, materials with high dielectric constants will have a low degree of absorption, and therefore a high degree of transparency, as the objective light will make it through the material without absorption loss. Effectively, the photons of light can escape more unscathed than they would in a material with a lower dielectric constant. And since dielectric constant is related to refractive index as shown above, materials with a high refractive index will also be highly transparent, and therefore of great use in microscopy/optical techniques.

Refractive indices of clearing agent and mounting solutions of the invention are disclosed in Table 1.

TABLE 1

Refractive indices of various clearing agent and mounting solutions of the invention.

| Clearing Agent and Mounting Solution Formulation[1] | Refractive Index |
| --- | --- |
| TCE-34.5%; Glyc- 12%; HCl (34%)- 1.5%; H$_2$O- 28%; MeOH- 24% | 1.4155 |
| TCE- 45%; Glyc- 10%; HCl - 1.25%; H$_2$O - 23.75%; MeOH-20% | 1.4310 |
| TCE- 27.4%; Glyc- 8.3%; TCAA- 0.7%; MeOH- 14.2%; LA- 49.4% | 1.4370 |

TABLE 1-continued

Refractive indices of various clearing agent and mounting solutions of the invention.

| Clearing Agent and Mounting Solution Formulation[1] | Refractive Index |
|---|---|
| TCE-56.25%; Glyc-12.5%; TCAA-1.25%; H$_2$O - 30% | 1.4315 |
| TCE- 27.4%; Glyc- 8.3%; TCAA- 0.7%; MeOH- 14.2%; DMSO- 49.4% | 1.4640 |
| TCE-94%; TCAA-5%; NaOH-1% | 1.4880 |
| TCE- 91%; Glyc- 3.3%; TCAA- 0.3%; MeOH- 5.4% | 1.4875 |
| TCE- 27.4%; Glyc- 8.3%; TCAA- 0.7%; MeOH- 14.2%; Tol- 49.4% | 1.4770 |
| TCAA-6%; NaOH- 4%; H$_2$O - 90% | 1.4280 |
| TCE- 97%; TCAA-3% | 1.4885 |
| TCE- 63.0%; Glyc-13.2%; TCAA- 1.1%; MeOH-22.7% | 1.4565 |
| TCE- 27.4%; Glyc-8.3%; TCAA- 0.7%; MeOH-63.6% | 1.3895 |
| TCE- 27.4%; Glyc- 8.3%; TCAA- 0.7%; MeOH- 14.2%; CWO- 49.4% | 1.4790 |
| TCE- 54.8%; Glyc- 16.6%; TCAA- 1.4%; MeOH- 27.2% | 1.4450 |

[1]TCE = trichloroethanol, TCAA = trichloroacetic acid, Glyc = glycerol, MeOH = methanol, NaOH = sodium hydroxide, LA = lactic acid, DMSO = dimethylsulfoxide, Tol = toluene, CWO = cedar wood oil. All percentages are v/v.

A number of analog structures have been provided which can be used as a substitute for trichloroethanol (FIG. 10). 2-chloroacetaldehyde dimethyl acetal has been shown to be effective at the same concentrations as trichloroethanol, although the refractive index is only 1.3810, at the low end of the desired range. One way to achieve the desired refractive index is to incorporate a clearing agent having one or more halogens (F, Cl, Br, I) in a carbon skeleton which also contains a water solubilizing group capable of hydrogen bonding. For example, the carbon skeletons can be selected from any mono- or poly-halogenated branched or unbranched alcohol, diol, glycol, aldehyde, aldehyde-hydrate, hemi-acetal, acetal, ketal, aminal, or hemi-aminal of C1-C20 family, where branches are defined as any mono- or poly-halogenated aliphatic or aromatic side chains containing hydroxyl, amino, ether, carboxyl, carboxyamido, carbonate, carbamyl, carbonyl-chloride, polyethylene-glycol, or aminoethanol groups, and any polymeric arrangement of such derivatives.

In comparative qualitative examinations, the clearing agent and mounting solutions of the invention perform as well as or better than acidified chloral hydrate, which is a DEA scheduled substance under US law, requiring DEA approval and compliance in order to purchase, possess or use the compound. In quantitative examinations, the clearing agent and mounting solution of the invention has matched or outperformed the chloral hydrate-based solutions, and exhibited a refractive index greater than chloral hydrate solution, the universal standard. This invention can be used as a clearing agent and mounting solution to identify the same anatomical characteristics or diagnostic features that are employed for the identification of different plant, microbial, animal, and earth science materials, without losing clarity, definition or resolution of the objective structures.

For example the clearing agent and mounting solutions of the invention are useful for microscopic identification of different plants, plant parts, animals and microbial materials. The clearing agent and mounting solutions can be used with any living organisms such animals, fungi, protists and bacteria and even with blood and plasma samples, as a mounting medium in microscopy and/or other optical techniques with applications in forensics, and biology and earth sciences. The inventive solutions can be used to clear specimens, rendering them transparent; these specimens can later be differentially stained and high quality images obtained. The inventive clearing agent and mounting solutions and semi permanent mounting media can also be used with non-living materials, including but not limited to soil particles and geological samples.

The inventive clearing agent and mounting solutions are useful not only for botanical microscopy but also for mycology, entomology, histology, food science, quality control (identification of living organisms for manufacture of pharmaceuticals, excipients, dietary products, adulterations, misidentifications, contaminations), forensics, nematology, virology, immunology, mineralogy, microscopy including but not limited to differential interference contrast microscopy, electron microscopy, and other related applications of microscopy and optics.

Figure 11:
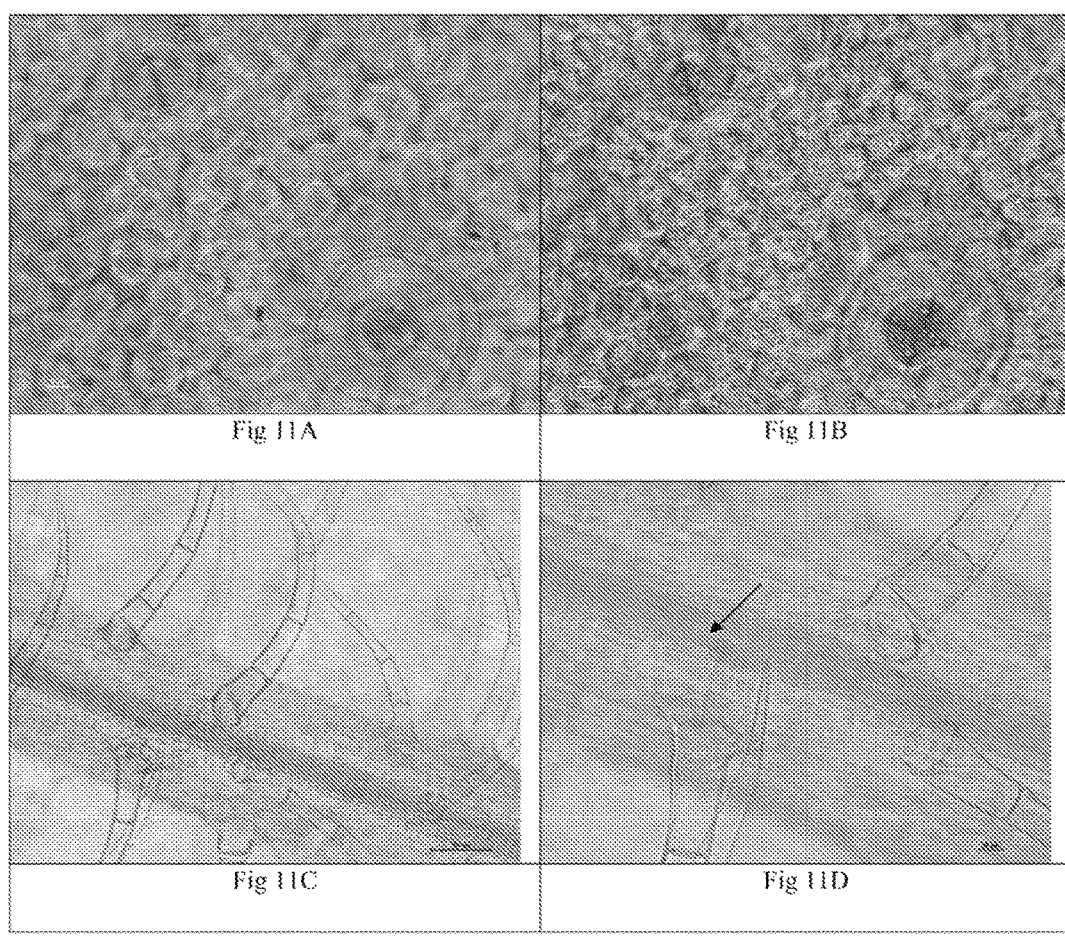
FIG. 11 displays fresh whole mounted specimens cleared with Example 1 clearing agent and mounting solution. A-B: Basil leaf; C-F: Oregano leaf; G-H: *Arabidopsis thaliana* root.
Figure 11:
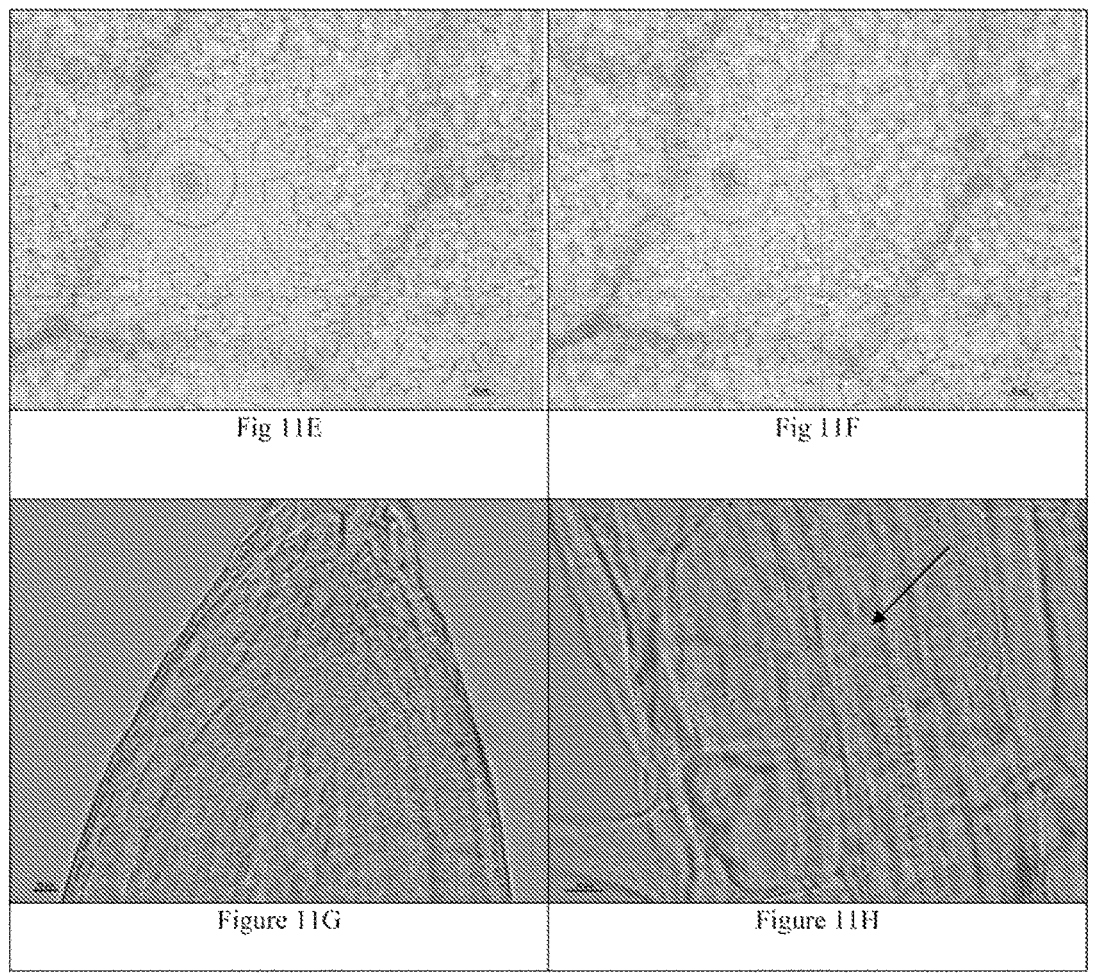

For example, one application of the inventive clearing and mounting solution is in quality assessment of commercial herbal products. It has also been determined that the inventive solutions are useful for clearing whole mounted dried, partially dry and fresh materials. For example, in basil, the oil glands, epidermis with stomata and underlying palisade cells could be observed (FIG. 11 A, B). In oregano, the epidermis over the vein with covering trichomes, capitates and peltate oil glands was distinguished (FIG. 11 C-F). Details of the cellular organization of the root apical meristem in *Arabidopsis thaliana* can be observed after clearing with this invention (FIG. 11 G-H). In addition, a number of other herbs and spices (dry samples and whole tissues) were analyzed subsequently using the invention as clearing reagent with comparable results.

The solutions of the invention penetrate into tissues and render them more transparent, as does acidified chloral hydrate solution. After treatment with a clearing agent of the invention, samples are cleared, which allows internal as well as surface details to be easily identified. This feature is most significant when it is used with whole mount tissues in which different layers of the transparent tissues are observed without the need for sectioning or remounting. Clear tissues also allow for staining techniques to more effectively highlight diagnostic features in only one single step without requiring dehydration of the tissues or pre-treatment of the tissues (FIG. 11).

Figures 12, 13, 14, 15, 16, 17:
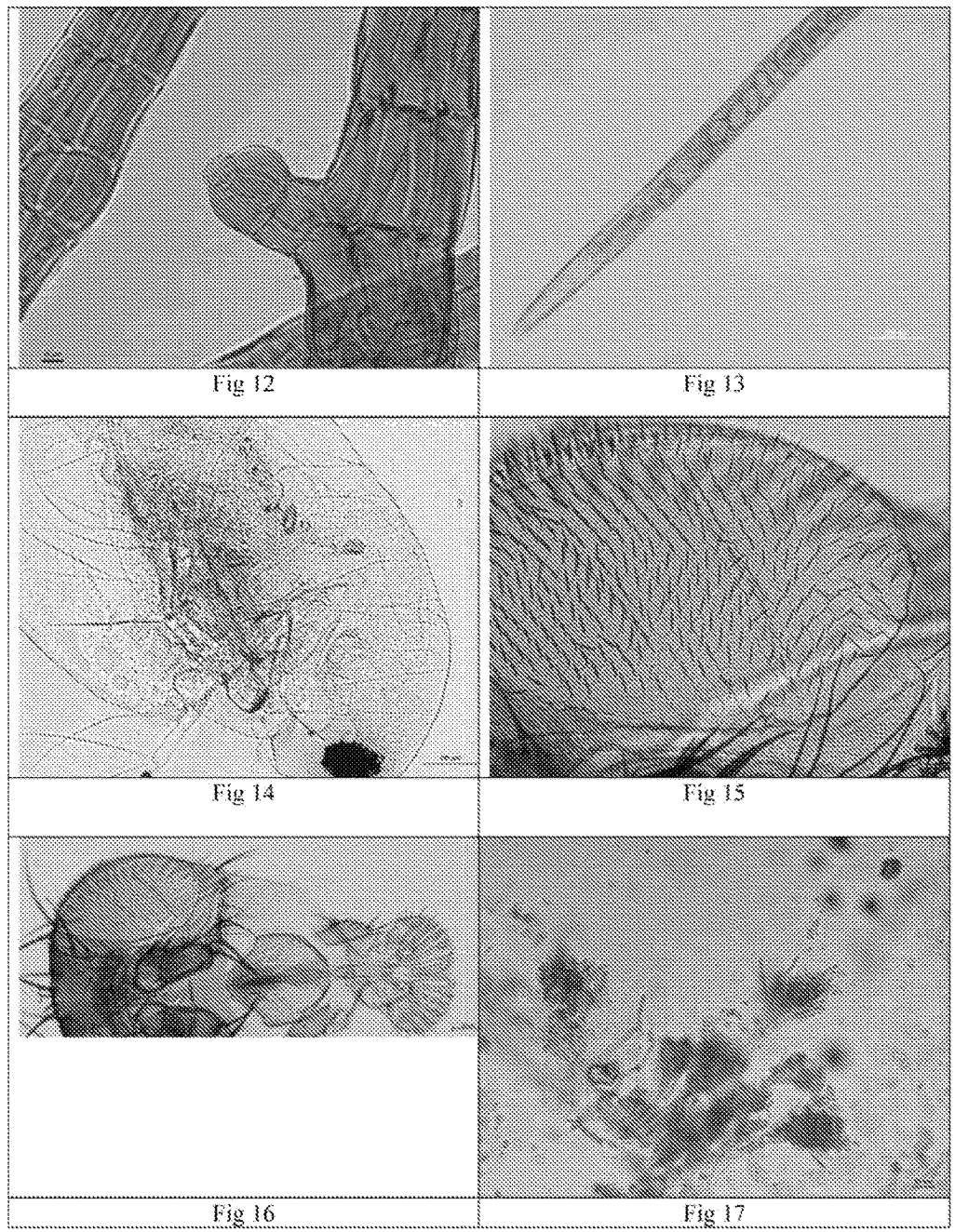
FIG. 12 shows a red alga *Polysiphonia* sp gametophyte showing a secondary branch forming off the main axis, cleared with Example 1 clearing agent and mounting solution.
FIG. 13 shows a roundworm free living nematode *Panagrellus redivivus* (Animalia) anterior end showing internal structures, cleared with Example 1 clearing agent and mounting solution.
FIG. 14 shows a small aquatic crustacean *Daphnia* sp. (Animalia) anterior end showing internal structures, cleared with Example 1 clearing agent and mounting solution.
FIG. 15 shows a characteristic *Drosophila melanogaster* (Animalia) compound eye, cleared with Example 1 clearing agent and mounting solution.
FIG. 16 shows a dorsal view of the head of *Drosophila melanogaster* (Animalia) showing compound eye, antenna and mouth parts, cleared with Example 1 clearing agent and mounting solution.
FIG. 17 shows the fungus *Penicillium* sp. conidiophores with a chain of conidia (asexual spores) at the end, cleared with Example 1 clearing agent and mounting solution.

The inventive solutions are also effective to clear protists, animals including but not limited to red algae (FIG. 12), round worms (*Panagrellus redivivus*, FIG. 13), water fleas, *Daphnia* sp (FIG. 14), and fruit flies (*Drosophila melanogaster*, FIGS. 15 and 16).

Figures 18, 19, 20, 21:
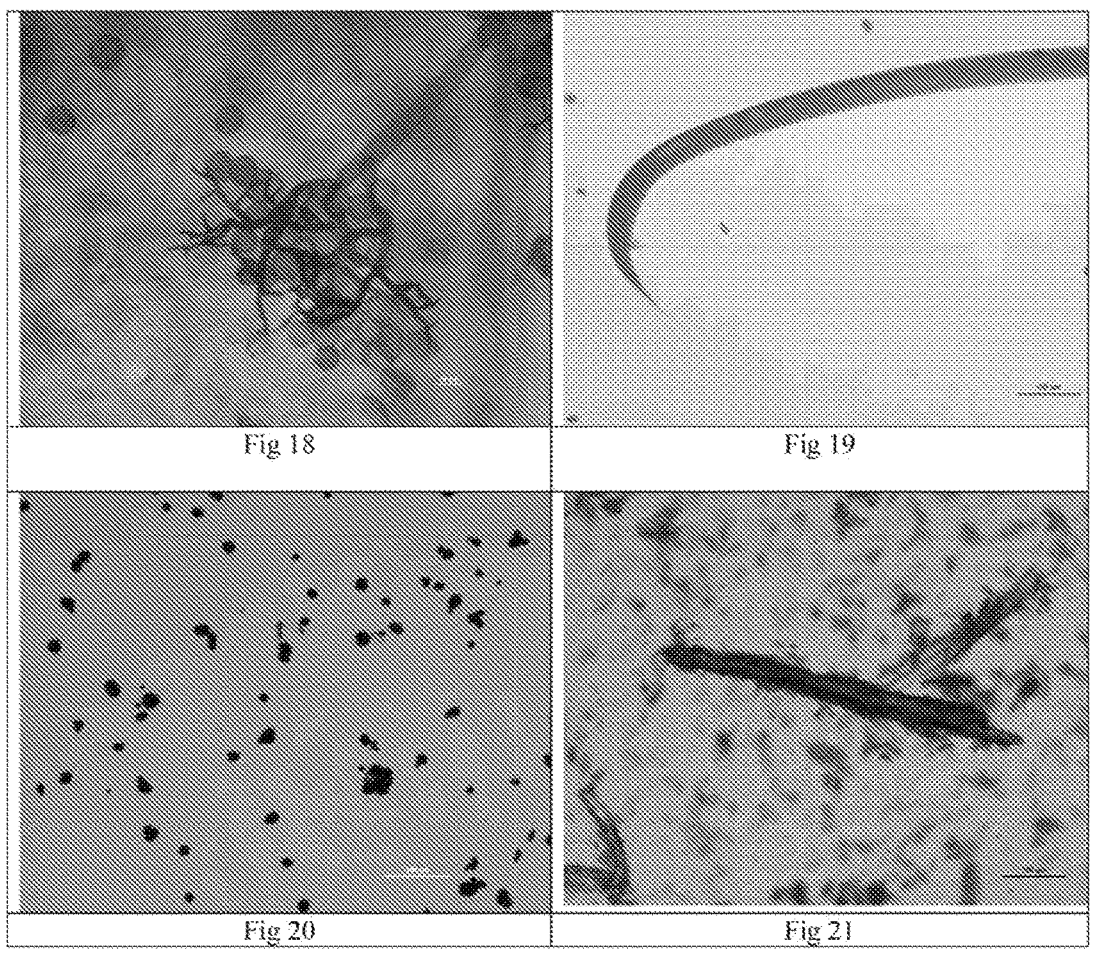
FIG. 18 shows basil downy mildew (*Peronospora belbahrii*), stained with iodine solution and sulfuric acid, cleared with Example 1 clearing agent and mounting solution.
FIG. 19 shows a roundworm *Panagrellus redivivus* (Animalia.) stained with fuchsine, cleared with Example 1 clearing agent and mounting solution.
FIG. 20 shows characteristic starch grains of Ginger (*Zingiber officinale*) stained with iodine solution, cleared with Example 1 clearing agent and mounting solution.
FIG. 21 shows characteristic lignified fibers of *Prunus africana* stained with phloroglucinol/HCl solution, cleared with Example 1 clearing agent and mounting solution.

In order to identify different components in the cells, quite frequently tissues are stained. There are several staining combinations available to enhance the details between different components of the cells. Stains are selected to provide the maximum contrast between particular structures based on their chemical composition. Much of the success of the images obtained after staining is due to the clearing agent used as a pretreatment. The solutions of the present invention also have no interference with the major stains used for particular structures. As examples, *penicillium* sp was first cleared with an inventive clearing agent and then stained with a solution of aniline blue in lactic acid (FIG. 17), downy mildew became dark brown after staining with iodine solution and sulfuric acid (FIG. 18), the round worm *Pangrellus redivivus* stained pink/red with fuchsine (FIG. 19), starch grains were stained black with iodine solution in ginger rhizome dry samples (FIG. 20) and sclereids fibers were stained red with phloroglucinol/HCl solution (FIG. 21).

EXAMPLES

General Procedures
Preparation of Plant Specimens

Plant materials were dried or used fresh. Dried plant materials were ground to a fine powder using a commercial coffee grinder.

Mounting of Specimens for Microscopy

A small quantity of fine powder material was spread on a microscope slide, and mounted with two drops acidified chloral hydrate solution (control), or mounted with two drops of the clearing agent and mounting solution of Example 1 and a cover slip was attached. Then the slide was heated on a hot plate (medium temperature) for 30-60 sec until the clearing agent and mounting solution boiled. The microscopic analysis was conducted using a Nikon eclipse 80i microscope, with the imaging software NIS D 3.00 SP7. Differences or similarities in diagnostic features or characteristics for each sample were recorded. Fresh specimens were submerged in the clearing agent and mounting solution until they were transparent, usually taking around 20-30 minutes depending the thickness of the material. Larger samples may require up to 2-3 days. Once the material was cleared, it was mounted on a microscope slide with one or two drops of this invention and a cover slip was added. Fresh specimens were cleared and transparent, allowing the visualization of deeper layers of tissues without losing clarity.

For staining the materials, first the material was cleared as mentioned above, cover slip was removed, one or two drops of the stain was added waited for few minutes and finally the cover slip was applied.

Example 1. Preparation of a Clearing Agent and Mounting Solution of the Invention 4.5 mL of 2,2,2-trichlorethanol (Sigma-Aldrich, 99%, reagent grade) was thoroughly mixed with 1.0 mL of glycerol. To this homogenous solution was added 2.5 mL of a 4% (m/v) aqueous solution of 2,2,2-trichloroacetic acid, at which time cloudiness was observed. The solution was mixed thoroughly until completely clear, about 5 minutes.

Figure 2:
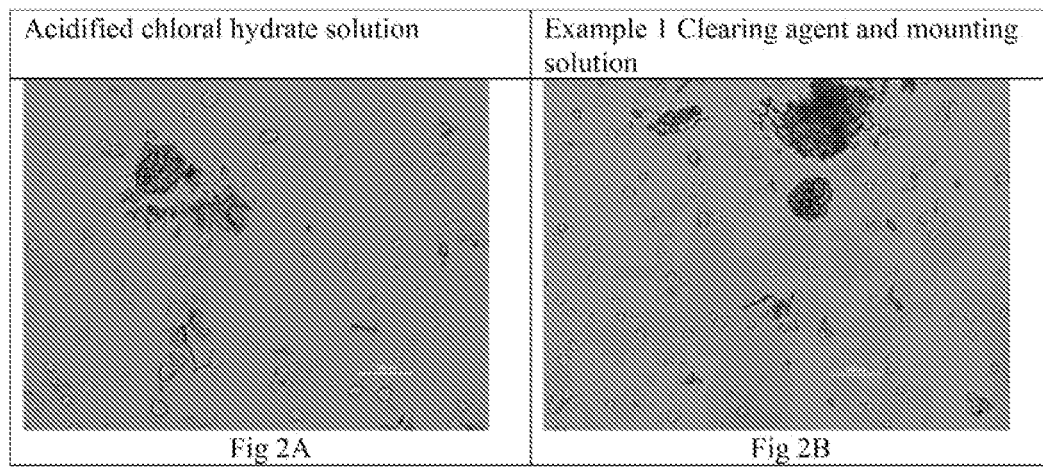
FIG. 2 shows a microscopic view of abundant starch grains of ginger, *Zingiber officinale* Roscoe (Zingiberaceae); comparison of acidified chloral hydrate solution versus Example 1 solution.
Figure 3:
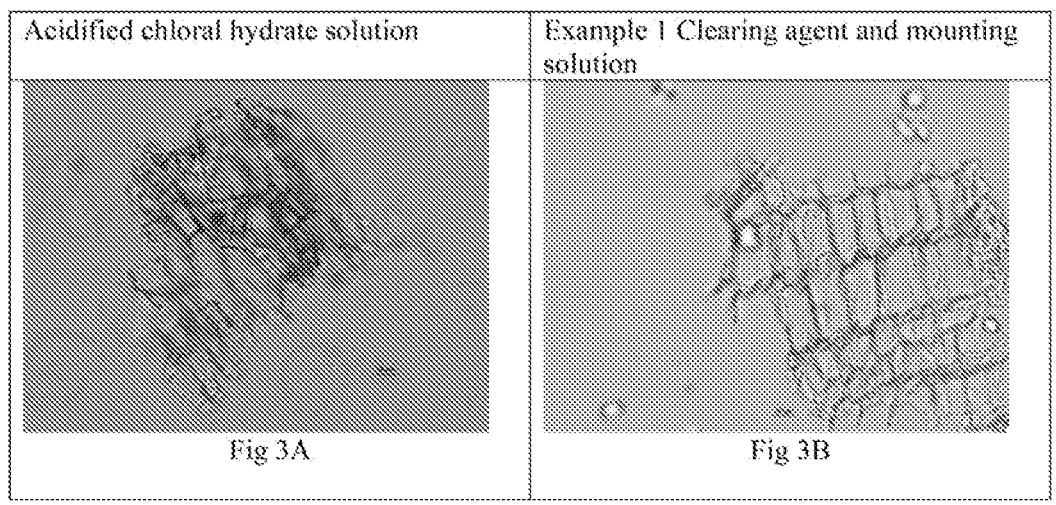
FIG. 3 shows a microscopic view of ginger epidermis and parenchyma cells, *Zingiber officinale* Roscoe (Zingiberaceae); comparison of acidified chloral hydrate solution versus Example 1 solution.

Example 2. Ginger (Rhizome), *Zingiber officinale* Roscoe (Zingiberaceae); FIGS. 1-3

Powdered ginger samples are characterized by numerous fragments of isodiametric thin-walled parenchyma cells containing starch granules; fragments of thin-walled fibers with oblique slit-like pits; fragments of scalariform, reticulate, and spiral vessels, thin-walled cells with suberized radial walls; numerous starch granules with various forms such as simple, flat, oval, oblong with terminal protuberance.

In ground ginger samples, fragments of parenchyma cells, cell with circular striations (cork cells), fibers accompanied by vessels and abundant starch grains the compact epidermal cells with sharp edges can be observed using the clearing agent and mounting solution of the invention. There was no difference in the structures observed between the inventive and standard clearing agent and mounting solutions.

FIG. 1 shows a microscopic view of characteristic annular vessel elements and fibers of ginger: FIG. 1A, ginger characteristic annular vessel element and fibers using acidified chloral hydrate solution; FIG. 1B, ginger characteristic annular vessel element with fibers and abundant starch grains attached to the fibers using clearing agent and mounting solution of Ex 1.

FIG. 2 shows a microscopic view of abundant starch grains of ginger. More starch grains can be observed using the clearing agent and mounting solution of Example 1, versus acidified chloral hydrate solution: FIG. 2A, ginger sample with characteristic abundant starch granules, mostly simple, using acidified chloral hydrate solution; FIG. 2B, ginger sample with abundant starch grains using clearing agent and mounting solution of Ex 1.

FIG. 3 shows a microscopic view of ginger epidermis and parenchyma cells. There is no difference in the structures observed using the inventive solution, versus acidified chloral hydrate solution: FIG. 3A, group of compact epidermal cells using acidified chloral hydrate solution; FIG. 3B, group of compact epidermal cells using clearing agent and mounting solution of Ex 1.

Example 3. Mate (Leaves), *Ilex paraguariensis* (Aquifoliacea); FIGS. 4-7

Ground *Ilex* leaves are characterized by upper epidermis composed by polygonal cells with unevenly thickened walls. Lower epidermis cells are smaller than those of the upper epidermis, and thinner cell walls, cuticular striations are well marked. Stomata anomocytic (epidermal cells surrounding the guard cell pair are not morphologically distinct from the other epidermal cells). Groups of lignified fibers are visible.

Figure 4:
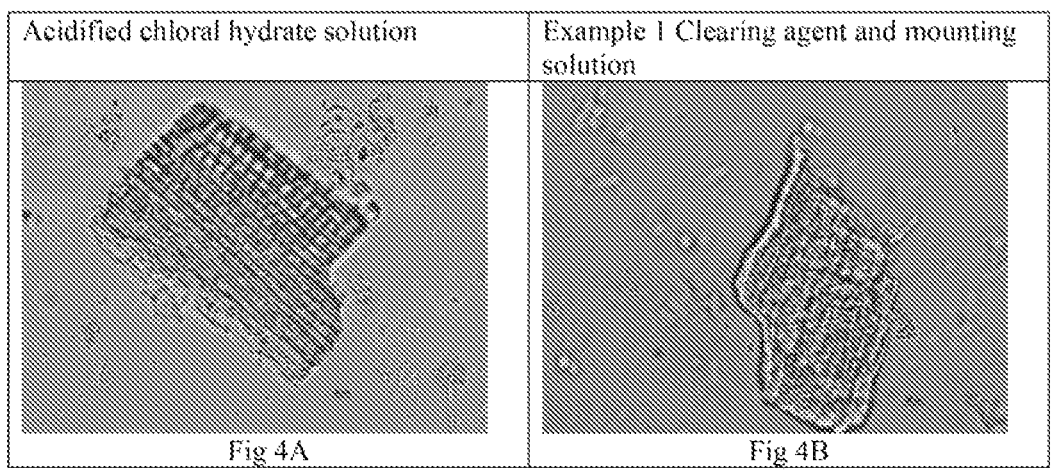
FIG. 4 shows a microscopic view of fragments of epidermis over leaf veins, Mate (leaves), *Ilex paraguariensis* (Aquifoliacea); comparison of acidified chloral hydrate solution versus Example 1 solution.

FIG. 4 shows a microscopic view of fragments of epidermis over leaf veins. The upper epidermis is composed of polygonal cells with unevenly thickened walls. Stomata are absent in the upper epidermis. There are no differences observed using the inventive solution, versus acidified chloral hydrate solution: FIG. 4A, fragment of polygonal cells of the upper epidermis over the vein using acidified chloral hydrate solution; FIG. 4B, fragments of polygonal cells of the upper epidermis over the vein using clearing agent and mounting solution of Ex 1.

Figure 5:
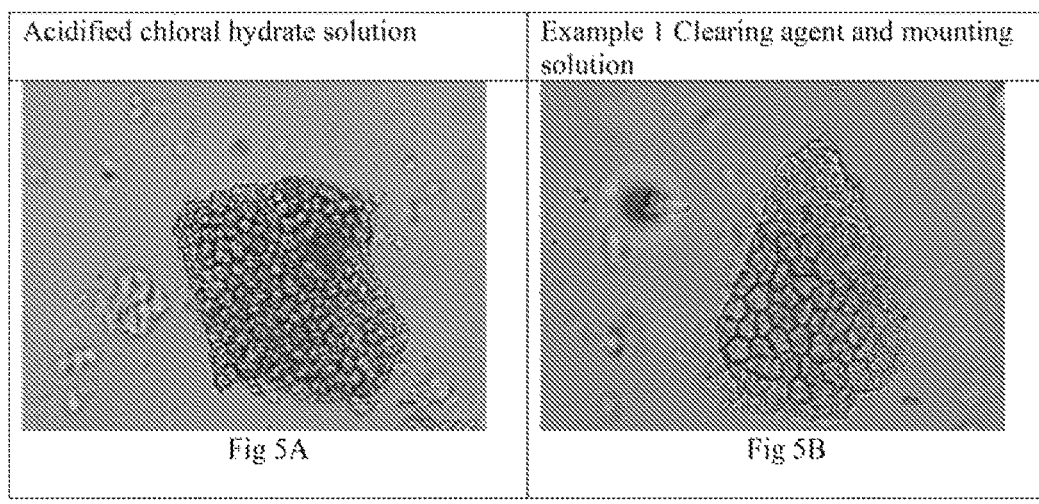
FIG. 5 shows a microscopic view of the upper epidermis underlying palisade cells, Mate (leaves), *Ilex paraguariensis* (Aquifoliacea); comparison of acidified chloral hydrate solution versus Example 1 solution.

FIG. 5 shows a microscopic view of the upper epidermis underlying palisade cells, large and closely packed. Circular striations can be observed. Those cells treated with the invented solution are less obscured versus those treated with acidified chloral hydrate solution: FIG. 5A, fragment of upper epidermis underlying parenchyma cells, cuticle is irregular striated, using acidified chloral hydrate solution; FIG. 5B, fragment of upper epidermis underlying parenchyma cells, cuticle is irregular striated, using clearing agent and mounting solution of Ex 1.

Figure 6:
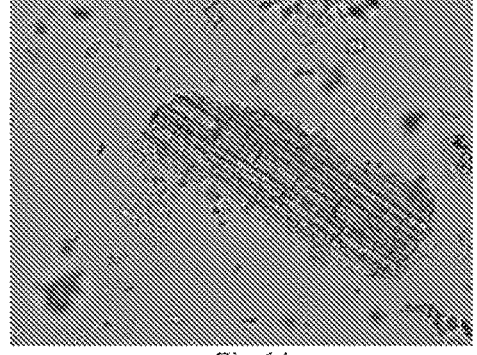
FIG. 6 shows a microscopic view of fragments or groups of pericycle of fibers, Mate (leaves), *Ilex paraguariensis* (Aquifoliacea); comparison of acidified chloral hydrate solution versus Example 1 solution.

FIG. 6 shows a microscopic view of fragments or groups of pericycle of fibers. Fibers are lignified, moderately thickened and have pitted walls (gap in the internal secondary thickening of the cell wall). Pits from the fibers in FIGS. 6A and 6B can be clearly observed with both clearing agent and mounting solutions: FIG. 6A, longitudinal view of a vein section showing fibers which have thickened walls with rounded or slit shaped pit (gap in the internal secondary thickening of the cell wall), using acidified chloral hydrate solution; FIG. 6B, longitudinal view of a vein section showing fibers which have thickened walls with rounded or slit shaped pit (gap in the internal secondary thickening of the cell wall), using clearing agent and mounting solution of Ex 1.

Figure 7:
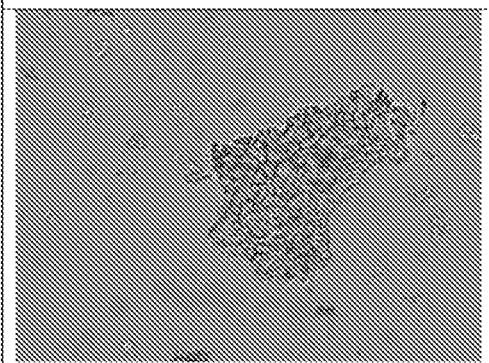
FIG. 7 shows a microscopic view of the lower epidermis showing characteristic anomocytic stomata, Mate (leaves), *Ilex paraguariensis* (Aquifoliacea); comparison of acidified chloral hydrate solution versus Example 1 solution.

FIG. 7 shows a microscopic view of the lower epidermis showing characteristic anomocytic stomata. There was no difference between the clearing agent and mounting solutions in clarity and function: FIG. 7A, lower epidermis surface showing anomocytic stomata and circular cuticular striations, using acidified chloral hydrate solution; FIG. 7B, lower epidermis surface showing anomocytic stomata and circular cuticular striations, using clearing agent and mounting solution of Ex 1.

Figure 8:
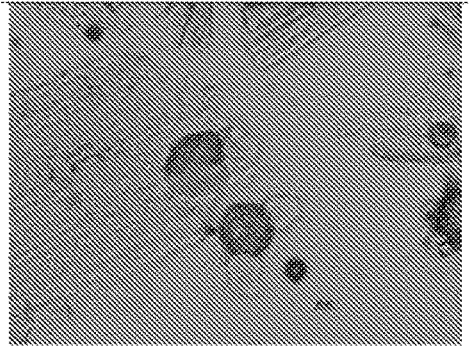
FIG. 8 shows a microscopic view of rounded or elliptical pollen grains with three germinal pores, exine (outermost cell wall of pollen grain) dentate spinose, Safflower (flower), *Carthamus tinctorius* L. (Asteraceae); comparison of acidified chloral hydrate solution versus Example 1 solution.
Figure 8:
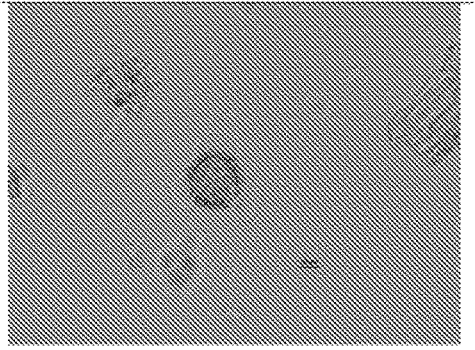
Figure 9:
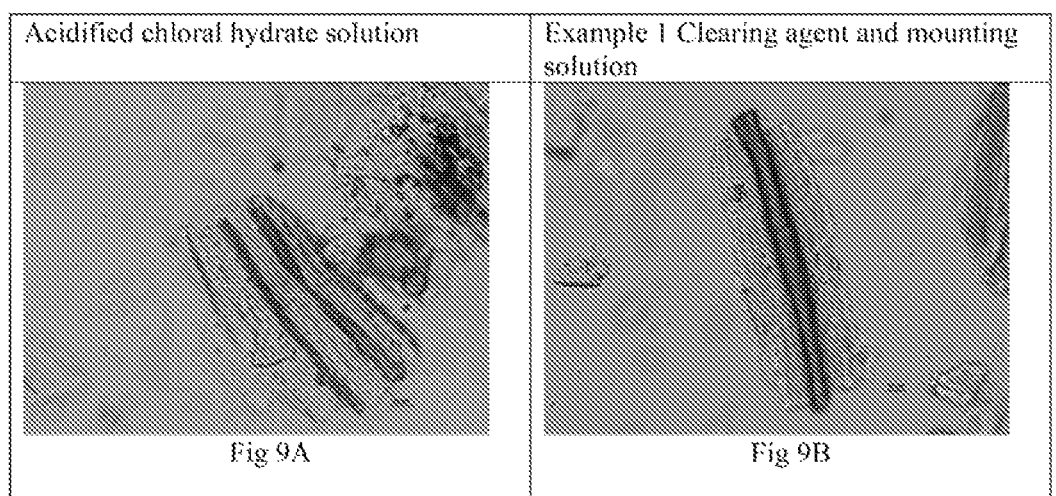
FIG. 9 shows a microscopic view of laticiferous ducts (tubular cells containing latex fluid) with a reddish-brown secretion next to vessels elements, Safflower (flower), *Carthamus tinctorius* L. (Asteraceae); comparison of acidified chloral hydrate solution versus Example 1 solution.

Example 4. Safflower (Flower), *Carthamus tinctorius* L. (Asteraceae); FIGS. 8-9

Powdered samples of flowers from Safflower have the abundant pollen grains with three noticeable germinal pores. The exine (outer coat of the pollen grain) is dentate and spinose. The presence of laticferous ducts with a reddish brown secretion next to vessels was observed. In ground samples of safflower, pollen grains with three germinal pores, exine and laticiferous ducts with a reddish-brown secretion next to vessels could be observed.

FIG. 8 shows a microscopic view of rounded or elliptical pollen grains with three germinal pores, exine (outermost cell wall of pollen grain) dentate spinose: FIG. 8A, characteristic pollen grain with three germinal pores, exine dentate, using acidified chloral hydrate solution; FIG. 8B, characteristic pollen grain with three germinal pores, exine dentate, using clearing agent and mounting solution of Ex 1.

FIG. 9 shows a microscopic view of laticiferous ducts (tubular cells containing latex fluid) with a reddish-brown secretion next to vessels elements. There were no differences observed using clearing agent and mounting solution, versus acidified chloral hydrate solution: FIG. 9A, two laticiferous ducts with a darker secretion next to the vessel elements, using acidified chloral hydrate solution; FIG. 9B, laticiferous duct filled with a darker secretion next to the vessel elements, using clearing agent and mounting solution of Ex 1.

FIG. 11 displays fresh whole mounted plant specimens cleared with Example 1 clearing agent and mounting solution. A-B: Basil leaf. A, epidermis with diacytic stomata, capitate and peltate glands; B: mesophyll cells with chloroplasts; C-F: Oregano leaf. C, covering trichomes with thick cell walls over the vein and capitate glands; D, Close up of capitate glands (arrow); E: depicting epidermis and peltate oil gland; F: mesophyll cells; G-H: *Arabidopsis thaliana* root; G, root tip cellular differentiation; H: xylem differentiation in root.

The clearing and mounting solution and its derivatives and/or analogs can also be used effectively in the same or a similar manner with cells or tissues from animals including, without limitation, poultry, humans, livestock, reptiles, amphibians, insects and mites, as well as protists, mold, fungi, bacteria, and other microorganisms.

The specimens displayed in FIGS. 12-21 were prepared analogously to those above, using the clearing and mounting solution of Example 1.

FIG. 12 shows a red alga *Polysiphonia* sp gametophyte showing a secondary branch forming off the main axis.

FIG. 13 shows round worm free living nematode *Panagrellus redivivus* (Animalia) anterior end showing internal structures (buccal cavity and juveniles hatched internally).

FIG. 14 shows a small aquatic crustacean *Daphnia* sp. (Animalia) showing anterior section FIG. 15 shows characteristic *Drosophila melanogaster* (Animalia) compound eye, showing numerous ommatidia (light detectors).

FIG. 16 shows a dorsal view of the head of *Drosophila melanogaster* (Animalia) showing compound eye, antenna and mouth parts.

FIG. 17 shows fungus *Penicillium* sp. conidiophores with a chain of conidia (asexual spores) at the end.

FIG. 18 shows basil downy mildew (*Peronospora belbahrii*), protist, with distinct staining of characteristic branched conidiophores and conidia after one week of inoculation. Stained with iodine solution and sulfuric acid.

FIG. 19 shows a round worm *Panagrellus redivivus* (Animalia) stained with fuchsine.

FIG. 20 shows characteristic starch grain of Ginger stained with iodine solution.

FIG. 21 shows characteristic lignified fiber of *Prunus africana* stained with phloroglucinol/HCl solution.

The present invention has been described and exemplified with the specific embodiments disclosed above, and in the following claims, which are not intended to limit the scope of the invention in any way.

All references cited herein are incorporated by reference in their entireties.

What is claimed is:

1. A clearing agent and mounting solution, comprising:
    (a) 10% to 97% (v/v) of trichloroethanol or derivative thereof;
    (b) 0% to 5% (v/v) trichloroacetic acid;
    (c) 12.5% to 50% (v/v) ethylene glycol, propylene glycol, polyethylene glycol, a polyethylene glycol derivative, or mixtures thereof, and/or derivatives thereof; and optionally water; wherein the refractive index of the solution is greater than or equal to 1.3810.

2. The clearing agent and mounting solution of claim 1, further comprising a C1-C6 alcohol.

3. The clearing agent and mounting solution of claim 2, wherein the C1-C6 alcohol comprises methanol, ethanol, or a mixture thereof.

4. The clearing agent and mounting solution of claim 1, wherein the trichloroethanol derivative comprises mono- and poly-halogenated branched and unbranched alcohols, dials, glycol aldehydes, aldehyde-hydrates, hemi-acetals, acetals, ketals, aminals, hemi-aminals of at least 2 carbon units, and polymers thereof; wherein the branches comprise mono- or poly-halogenated aliphatic or aromatic groups containing hydroxyl, amino, ether, carboxyl, carboxyamido, carbonate, carbamyl, carbonyl-chloride, polyethylene-glycol, or aminoethanol groups.

5. The clearing agent and mounting solution of claim 1, further comprising a solidification aid comprising polyethylene glycol, polyamide resin, polyvinylpyrrolidone, polyvinylalcohol, or mixtures thereof.

6. The clearing agent and mounting solution of claim 1, further comprising glycerol.

* * * * *